United States Patent
Ruebben

(10) Patent No.: US 10,653,870 B2
(45) Date of Patent: May 19, 2020

(54) CUTBACK METHOD FOR INTRAVASCULAR DILATION CATHETER

(71) Applicant: AACHEN SCIENTIFIC INTERNATIONAL PTE. LTD., Singapore (SG)

(72) Inventor: Alexander Ruebben, Monaco (MC)

(73) Assignee: Aachen Scientific International Pte. Ltd., Singapore (SG)

( * ) Notice: Subject to any disclaimer, the term of this patent is extended or adjusted under 35 U.S.C. 154(b) by 341 days.

(21) Appl. No.: 15/516,183

(22) PCT Filed: Oct. 2, 2014

(86) PCT No.: PCT/EP2014/071114
§ 371 (c)(1),
(2) Date: Mar. 31, 2017

(87) PCT Pub. No.: WO2016/050303
PCT Pub. Date: Apr. 7, 2016

(65) Prior Publication Data
US 2017/0291015 A1    Oct. 12, 2017

(51) Int. Cl.
*A61M 25/10* (2013.01)
*B29C 63/18* (2006.01)
(Continued)

(52) U.S. Cl.
CPC ....... *A61M 25/1029* (2013.01); *A61L 29/041* (2013.01); *A61M 25/1002* (2013.01);
(Continued)

(58) Field of Classification Search
CPC ............ A61M 25/104; A61M 25/0068; A61M 25/0169; A61M 25/0662; A61M 25/09;
(Continued)

(56) References Cited

U.S. PATENT DOCUMENTS 5,360,330 A * 11/1994 Jensen .................. B29B 13/025
                                                              425/144
6,613,067 B1 * 9/2003 Johnson ................ A61F 2/0095
                                                              604/103.11
(Continued)

FOREIGN PATENT DOCUMENTS

EP            1925332 A1      5/2008

OTHER PUBLICATIONS

International Search Report of the International Searching Authority with English Translation issued in the corresponding PCT International Application No. PCT/EP2014/071114, dated May 29, 2015 (8 pages).
(Continued)

*Primary Examiner* — Manuel A Mendez
(74) *Attorney, Agent, or Firm* — Raymond E. Ferrera; Adams and Reese LLP

(57) ABSTRACT

The invention relates to a method for producing a catheter (1) having a proximal segment, a distal segment, and an expandable element (2) arranged in the distal segment, it being possible to bring the expandable element (2) from a contracted state into an expanded state by supply of a fluid and there being arranged around the expandable element (2) in the contracted state a removable protector in the form of a tube (5), and the tube (5) being pulled over the expandable element (2) and being guided with the catheter (1) through one or more nozzles (6), stretching the tube (5) and reducing the inner diameter of the tube (5). Furthermore, the invention relates to a corresponding catheter (1) having a tube (5) pulled over the expandable element (2). The invention provides a catheter (1) having a particularly small cross section in the region of the distal segment.

11 Claims, 3 Drawing Sheets

(51) Int. Cl.
*A61L 29/04* (2006.01)
*B29C 63/00* (2006.01)
*B29K 27/18* (2006.01)
*B29L 31/00* (2006.01)

(52) U.S. Cl.
CPC ......... *A61M 25/1038* (2013.01); *B29C 63/18* (2013.01); *A61M 2025/1004* (2013.01); *A61M 2025/1031* (2013.01); *A61M 2025/1081* (2013.01); *B29C 63/0056* (2013.01); *B29K 2027/18* (2013.01); *B29L 2031/7542* (2013.01)

(58) Field of Classification Search
CPC .. A61M 25/00; A61M 25/10; A61M 25/1002; A61M 25/1029; A61M 29/02; A61M 25/1011; A61F 2/958; A61F 2/95; A61F 2/013; A61F 2/966; A61F 2/07; A61F 2/82; A61F 2/954; A61F 2/90; A61F 2/856; A61F 2/91; A61B 17/221; A61B 17/22032; A61B 17/22; A61B 17/320725; A61N 5/1002
See application file for complete search history.

(56) References Cited

U.S. PATENT DOCUMENTS

| | | | | |
|---|---|---|---|---|
| 7,309,324 B2* | 12/2007 | Hayes | ............... | A61M 25/104 |
| | | | | 604/96.01 |
| 8,808,238 B2* | 8/2014 | Tsubooka | ......... | A61M 25/1002 |
| | | | | 604/103.06 |
| 2008/0171977 A1* | 7/2008 | Blix | ..................... | A61M 25/10 |
| | | | | 604/96.01 |

OTHER PUBLICATIONS

Written Opinion of the International Search Authority (Form PCT/ISA/237) with English Translation issued in the corresponding PCT International Application No. PCT/EP2014/071114, dated May 29, 2015 (14 pages).

International Preliminary Report on Patentability Chapter I issued in the corresponding PCT International Application No. PCT/EP2014/071114, dated Apr. 4, 2017 (8 pages).

* cited by examiner

CUTBACK METHOD FOR INTRAVASCULAR DILATION CATHETER

The invention relates to a method for producing a catheter having a proximal segment, a distal segment, and an expandable element arranged in the distal segment, it being possible to bring the expandable element from a contracted state into an expanded state by supply of a fluid and there being arranged around the expandable element in the contracted state a removable protector in the form of a tube.

In percutaneous transluminal coronary angioplasty (PTCA), a dilation balloon catheter (dilation catheter, balloon catheter) having an expandable element (balloon) in its distal segment is used. Access to the cardiovascular system of the patient is achieved via an insertion instrument, usually in the groin via the femoral artery. The individual medical devices are inserted and advanced into the cardiovascular system of the patient in a percutaneous manner via the insertion instrument until the distal end is situated at the desired position. Specifically, a guide catheter is inserted, through which a guide wire and the balloon catheter are advanced. The guide wire is advanced first from the guide catheter; thereafter, the balloon catheter, which has a lumen to accommodate the guide wire, is moved distally via the guide wire until the balloon is situated at the site of the lesion, i.e., the vascular constriction (stenosis) to be eliminated. The balloon catheter has a supply lumen, which extends through the balloon catheter to the proximal end and is connected to the balloon at the distal end. As a result of supply of a fluid, the balloon is expanded at high pressure of at least 4 bar in general, from 8 to 12 bar in many cases, and so deposits in the region of the lesion are pressed against the inner wall of the artery in order thus to eliminate the stenosis and to improve blood flow. Subsequently, the balloon is folded up to give a small cross section, and so the balloon catheter can be removed from the vascular system of the patient and blood flow starts again through the widened artery.

Balloon catheters are, for example, known from the following US patent specifications: U.S. Pat. Nos. 4,762,129, 5,496,346 and 6,071,285.

Medical devices having a catheter and having an expandable element arranged in the distal segment are also used for widening stents. In this case, the primary action is not the pressing of deposits against the artery wall, but the radial expansion of the stent.

An important feature of a balloon catheter is its cross section, which is determined by the outer diameter of the distal segment of the balloon in the nonexpanded state. The outer diameter has an influence on how well the balloon catheter can be brought to the target site through the coronary arteries and across a tight lesion, a smallest possible outer diameter being desirable. Nevertheless, the possibility of expanding the balloon to the desired dimensions at the target site must be maintained. In this connection, U.S. Pat. Nos. 5,342,307 and 5,015,231 disclose a balloon protector sleeve around an at least triply folded balloon of a balloon catheter for angioplasty.

Reducing the diameter of the expanded part of the balloon catheter ("cut back") is important for balloon catheters and systems for implanting stents, because certain vascular constrictions (stenoses) are impassable for balloon catheters of normal diameter. It is therefore an object of the invention to provide a catheter having a minimized cross section in the distal segment in which the expandable element is situated. It is further an object of the invention to provide a method for producing a corresponding catheter.

According to the invention, this object is achieved by a method for producing a catheter having a proximal segment, a distal segment, and an expandable element arranged in the distal segment, it being possible to bring the expandable element from a contracted state into an expanded state by supply of a fluid and there being arranged around the expandable element in the contracted state a removable protector in the form of a tube, the tube being pulled over the expandable element and being guided with the catheter through one or more nozzles, stretching the tube and reducing the inner diameter of the tube.

According to the invention, a tube is pulled over the expandable element (balloon) and guided together with the catheter (balloon catheter) through a very narrow nozzle. In particular, the catheter can be pulled with the tube through the nozzle. In this way, the tube is stretched and fits tightly to the expandable element, and so the outer diameter of the catheter in the distal segment is greatly reduced. The tube thus forms an envelope around the expandable element. The balloon material of the expandable element is so tightly packed that the diameter is altogether only determined by the thickness of the materials used and not by any air pockets or tensions that erect the balloon again. In many cases, the expandable element is already laid in folds before the pulling-over of the tube in order to bring about a smallest possible cross section. The pulling-over of the tube brings about an additional compression and cross-section reduction. Typically, it is possible to bring about a reduction in the diameter to 4 French (1.33 mm) or less.

In many cases, it is useful to successively guide the balloon catheter with tube through nozzles of different diameter, the inner diameter decreasing from nozzle to nozzle. The catheter with tube is thus first brought to a first reduced diameter, before guidance through a nozzle of even smaller diameter is effected to achieve a second, further reduced diameter. In principle, this can be repeated in order to reduce the diameter even further, with guidance through nozzles of ever smaller inner diameter typically being effected not more than two to four times.

The catheter can comprise an inner tunnel or shaft, which typically extends through the interior of the catheter over a portion of the length or the entire length. The inner tunnel has a lumen for accommodating a guide wire, which lumen ends at the distal end of the catheter so that the guide wire can exit at the distal end. Fundamentally, various balloon catheters are known; in particular, a distinction is made between over-the-wire technology (OTW catheter) and rapid exchange (Rx catheter). Whereas in the case of the OTW catheter the guide wire extends through the entire volume, Rx catheters have a passage opening as access to the inner tunnel, through which opening the guide wire can exit proximal to the balloon, but distal to the proximal balloon catheter segment, which is a metallic hypotube in many cases. Likewise extending over the length of the balloon catheter is a supply lumen, through which a fluid can be guided to the actual balloon in order to widen it at the target site. Said supply lumen can, for example, be arranged around the inner tunnel or to the side thereof.

The nozzle can in principle have different shapes. What is important is that the cross section of the nozzle is chosen such that it is possible to tightly apply the tube to the expandable element. For example, the nozzle can be cylindrical, i.e., have the shape of a hollow cylinder, it being possible for the footprint of the cylinder to be a circle or an ellipse. In particular, the cylinder can be a straight cylinder, but a slanted cylinder is also conceivable in principle.

However, according to the invention, any desired opening which has a small inner diameter and which is capable of compressing catheter and tube to a desired extent is understood in principle to mean a nozzle. The length of the nozzle can vary; a certain length is not necessary, even a few millimeters may be sufficient. In practice, it is possible to take the approach of providing multiple openings having different diameters in a particular tool, and so, when catheter and tube are pulled through different openings, the diameter increasingly decreases. Pull-through can be carried out in a manual or automated manner.

The nozzle can also have a conical shape, i.e., the interior of the nozzle can have the shape of a cone or of a truncated cone. In particular, it is useful for a nozzle to become narrower from the inlet end to the outlet end in order to bring the expandable element, which is still relatively wide in the inlet region, to the final diameter.

To further improve the procedure, the nozzle can be heated during pull-through of the tube. After cooling, the tube additionally contracts somewhat further and thus ensures a further reduction in the cross section of the expandable element. Heating is effected to a temperature above room temperature, in particular to a temperature between 40 and 100° C., in particular between 50 and 80° C.

Furthermore, it is useful to suck out any air present from the expandable element before the tube is pulled over the distal segment, so that said air need not be pressed out during the compression process itself. Furthermore, it is advantageous when the expandable element is already laid in folds before the tube is pulled over, with 2 to 4 folds, in particular 3 folds, having being found to be especially useful. The step of laying in folds can be carried out in a manual or automated manner.

According to the invention, what is understood to be a tube is an envelope which is composed of a deformable material and which can be pulled over a portion of the catheter, especially the region of the distal segment in which the expandable element is situated. The tube is open on at least one side in order to allow it to be pulled over the catheter, but can also be open at both ends.

The tube should be manufactured from a material which generates a low friction, so that the material of the underlying expandable element is not damaged. Polytetrafluoroethylene (PTFE, Teflon) is especially suitable. However, the use of other materials is also possible, especially plastics materials having a low friction.

The tube must be pulled off immediately before use of the catheter. In this connection, it has been found that the expandable element decreases its cross section on a permanent basis as a result of fitting the tube, i.e., the expandable element remains tightly folded with minimal diameter until the element is expanded at the site of deployment by supply of a fluid under high pressure.

The invention has particular significance for active-ingredient-loaded balloons, also called drug-eluting balloons. Said balloons usually have a larger cross section than unloaded balloons, for example because an active ingredient such as paclitaxel is situated between the folds into which the balloon is laid in the contracted state. Especially in the case of very long balloons, this makes advancement in the blood vascular system difficult.

In addition to the method according to the invention, the invention also relates to the catheter itself, which is obtainable by the method according to the invention. The catheter comprises a proximal segment, a distal segment, and an expandable element arranged in the distal segment, it being possible to bring the expandable element from a contracted state into an expanded state by supply of a fluid. Furthermore, the catheter comprises a removable protector in the form of a tube which is arranged around the expandable element in the contracted state, the tube being pulled over the expandable element and being stretched longitudinally. Running longitudinally through the catheter up to the proximal end is a supply lumen, which is connected to the expandable element at the distal end and is used to supply a fluid for the expansion of the expandable element. Furthermore, the catheter can have an inner tunnel for accommodating a guide wire.

The proximal segment and the distal segment of the catheter can be manufactured from different materials in order to be able to use the balloon catheter optimally. Whereas a large flexibility is advantageous for the distal segment, so that the catheter can follow even narrow-lumen blood vessels in a problem-free manner without injuring said blood vessels, a higher rigidity is advantageous in the proximal region, so that it is possible to advance the catheter over relatively long distances. Accordingly, the proximal segment can be manufactured from metal, for example from stainless steel, whereas polymer materials such as polyamides, for example nylon, have been found to be useful for the distal segment. However, in principle, the invention also compasses balloon catheters in which proximal segment and distal segment are manufactured from the same material or in which proximal segment and distal segment ultimately do not differ in terms of structure and, accordingly, no transition between the segments can be discerned.

The invention will also be more particularly elucidated in the attached figures, in which.

Figure 1:
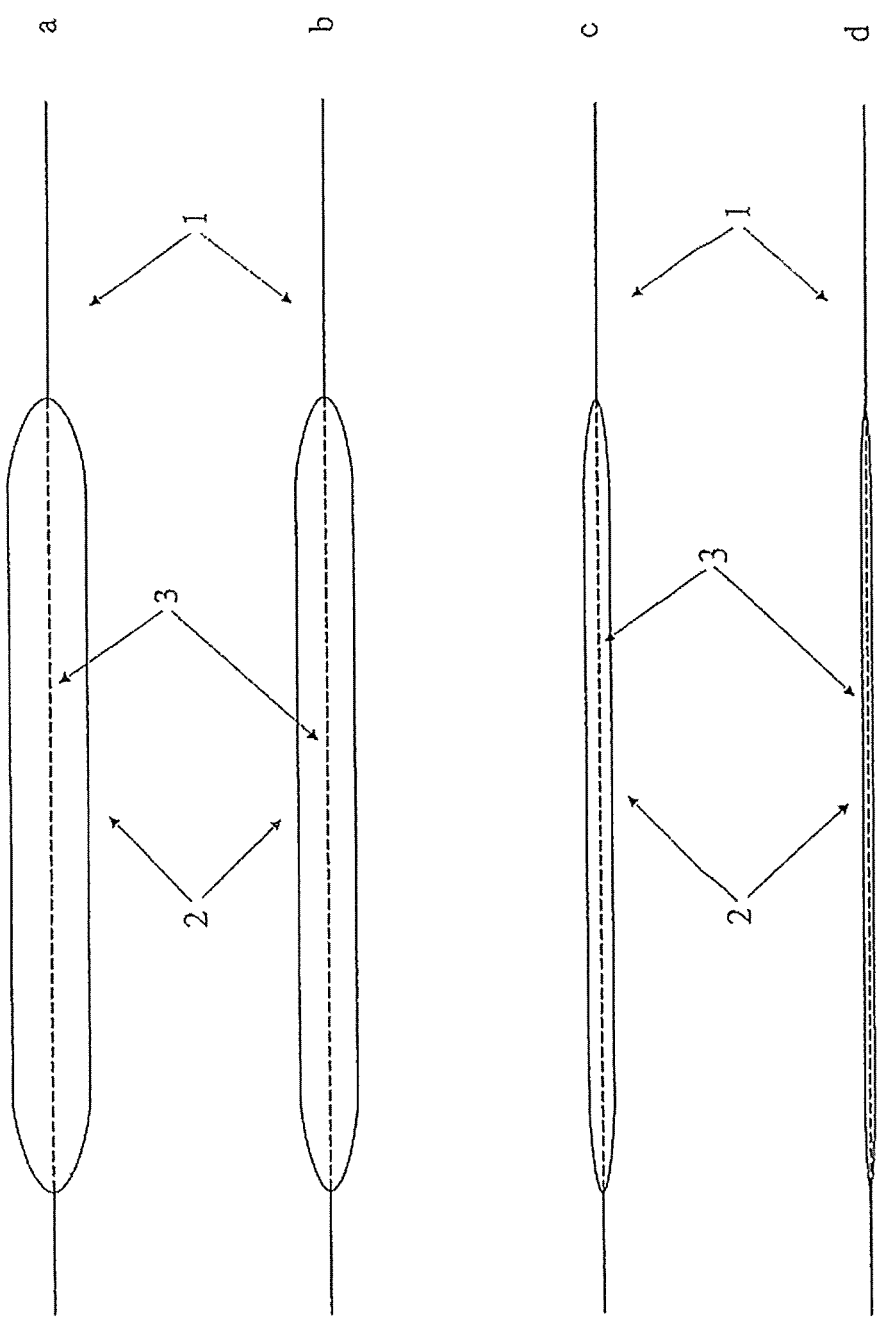
FIG. 1 shows a catheter according to the invention in lateral view.

FIG. 1 shows various depictions of the distal region of a balloon catheter 1 according to the invention. In its distal end-segment, the balloon catheter 1 has a balloon 2. Furthermore, the balloon catheter 1 has an inner tunnel 3, which also runs through the interior of the balloon 2.

In FIG. 1*a*, it is possible to identify the balloon 2 in the expanded state, after said balloon has been expanded by supply of a fluid under pressure. In this form, the balloon 2 is suitable for eliminating stenoses.

In FIG. 1*b*, it is possible to identify the balloon 2 in the nonexpanded state. Although the cross section of the balloon 2 is smaller than as per FIG. 1*a*, it is too large to be guided through narrow-lumen blood vessels.

FIG. 1*c* depicts the balloon 2 in the folded state, as corresponds to the prior art. In said state, the nonexpanded balloon envelope is folded up such that it fits tightly, and so the cross section is significantly reduced compared to FIG. 1*b*.

Lastly, FIG. 1*d* depicts the balloon 2 after application of the method according to the invention. Pulling over a tightly fitting tube and guidance through a nozzle ensures that the cross section of the balloon 2 decreases further and that the catheter 1 in the region of the balloon 2 has only a slightly larger diameter than in more proximal regions. The balloon 2 also maintains this small cross section when the tube is pulled off just before use.

Figure 2:
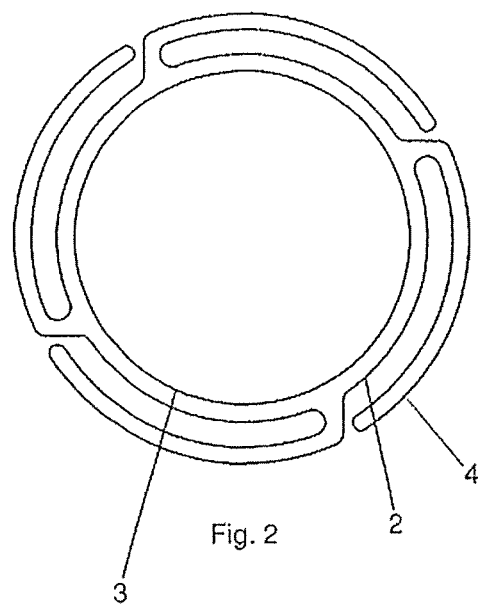
FIG. 2 shows a catheter according to the invention without tube in cross section.

FIG. 2 is a depiction of the balloon catheter 1 without tube in cross section. Here, the balloon 2 forms three folds 4, which are placed along the circumference in the same circumferential direction in order to thus ensure a tight fitting of the balloon 2 and a reduction in the diameter. The inner tunnel 3, which is part of the balloon catheter 1, runs through the interior of the balloon.

Figure 3:
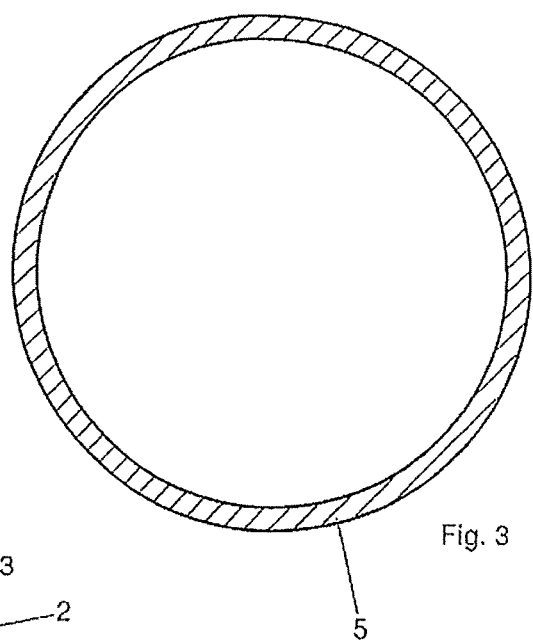
FIG. 3 shows a tube in cross section.

FIG. 3 depicts a tube 5, as can be used for being pulled over the balloon catheter 1. The tube 5 is manufactured from a material generating minimal friction with the surface of the balloon 2, especially from polytetrafluoroethylene.

Figure 4:
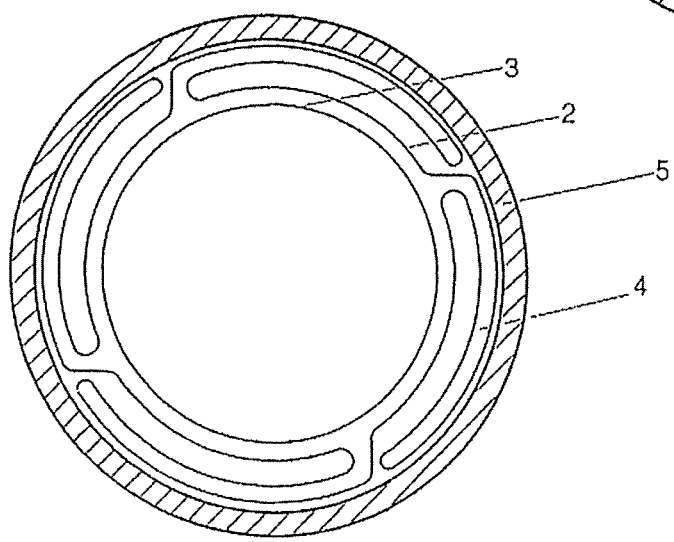
FIG. 4 shows a catheter according to the invention with tube in cross section and FIG. 5 shows the guidance of balloon and tube through a nozzle in longitudinal section.

FIG. 4 shows the balloon catheter 1, which has been covered with the tube 5, this being achieved in accordance with the invention by balloon catheter 1 and tube 5 being pulled together through a nozzle. The tube fits tightly to the balloon 2 and compresses said balloon even more, and so the cross section further decreases. While, for the sake of ease of identification, FIG. 4 still shows a certain distance between the tube 5, the individual folds 4 and the further regions of the balloon 2, these are in reality not present, i.e., all air pockets are practically completely removed, and so the cross section is altogether minimal.

Figure 5:
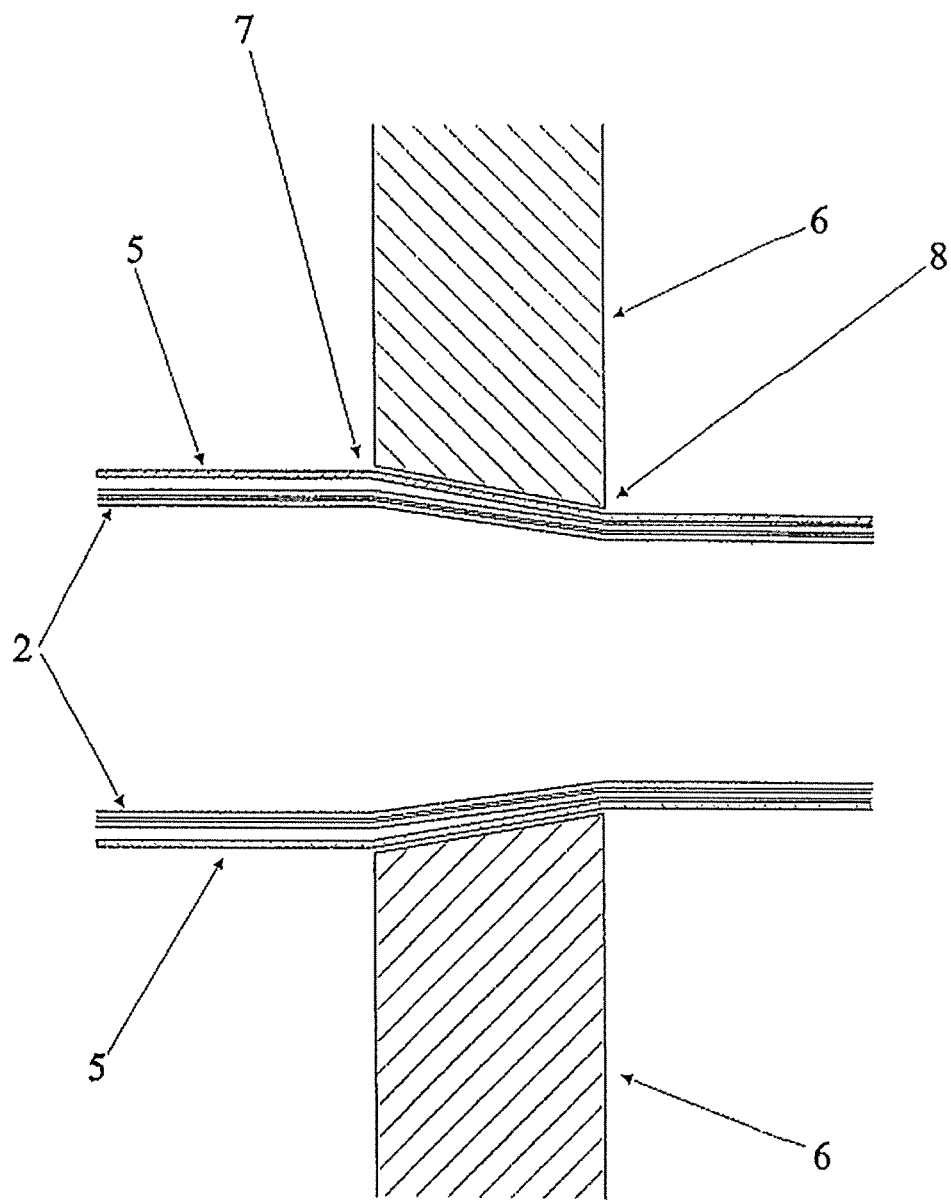

Lastly, FIG. 5 shows the guidance of the balloon 2, enveloped by the tube 5, through a nozzle 6, said guidance being effected from left to right in the depiction chosen here. The nozzle 6 has a larger cross section in the inlet region 7 than in the outlet region 8, i.e., the tube 5 and the various layers of the balloon 2 are pressed closer together, and so the balloon 2 enveloped by the tube 5 has altogether a smaller cross section after exit from the nozzle 6 than beforehand.

The invention claimed is:

1. A method for producing a catheter having a proximal segment, a distal segment, and an expandable element arranged in the distal segment, it being possible to bring the expandable element from a contracted state into an expanded state by supply of a fluid and there being arranged around the expandable element in the contracted state a removable protector in the form of a tube, wherein the tube is pulled over the expandable element and is guided with the catheter through one or more nozzles, stretching the tube and reducing the inner diameter of the tube.

2. The method as claimed in claim 1, wherein the nozzle has the shape of a hollow cylinder.

3. The method as claimed in claim 2, wherein the footprint of the cylinder is a circle of an ellipse.

4. The method as claimed in claim 1, wherein the nozzle is an opening in a tool.

5. The method as claimed in claim 1, wherein the nozzle has a conical shape.

6. The method as claimed in claim 1, wherein the catheter is successively guided together with the tube through multiple nozzles, the inner diameter of one nozzle being in each case smaller than the inner diameter of the nozzle through which the catheter was previously guided together with the tube.

7. The method as claimed in claim 1, wherein the nozzle is heated during pull-through of the tube.

8. The method as claimed in claim 1, wherein the tube is manufactured from polytetrafluoroethylene.

9. The method as claimed in claim 1, wherein the extendable element is laid in folds before pulling-over the tube.

10. A catheter obtainable by a method as claimed in claim 1, the catheter comprising a proximal segment, a distal segment, and an expandable element arranged in the distal segment, it being possible to bring the expandable element from a contracted state into an expanded state by supply of a fluid and there being arranged around the expandable element in the contracted state a removable protector in the form of a tube, the tube being pulled over the expandable element and being stretched longitudinally.

11. The catheter as claimed in claim 10, wherein the tube is manufactured from polytetrafluoroethylene.

* * * * *